(12) United States Patent
Vidalin

(10) Patent No.: US 6,599,491 B2
(45) Date of Patent: Jul. 29, 2003

(54) BIMODAL HYDROGEN MANUFACTURE

(76) Inventor: Kenneth Ebenes Vidalin, 760 World Trade Centre, 999 Canada Place, Vancouver, B.C. (CA), V8C 3E1

(*) Notice: Subject to any disclaimer, the term of this patent is extended or adjusted under 35 U.S.C. 154(b) by 0 days.

(21) Appl. No.: 09/768,030

(22) Filed: Jan. 22, 2001

(65) Prior Publication Data

US 2002/0098132 A1 Jul. 25, 2002

(51) Int. Cl.⁷ .............................. C01C 1/04; C01B 3/02; C01B 3/26
(52) U.S. Cl. .................... 423/359; 422/189; 423/648.1; 423/652
(58) Field of Search .............................. 423/359, 648.1, 423/650, 651, 652, 653, 654; 422/188

(56) References Cited

U.S. PATENT DOCUMENTS

| | | | |
|---|---|---|---|
| 4,175,115 A | | 11/1979 | Ball et al. |
| 4,315,900 A | * | 2/1982 | Nozawa et al. ............. 423/359 |
| 4,316,880 A | | 2/1982 | Jockel et al. |
| 4,367,206 A | * | 1/1983 | Pinto .......................... 423/359 |
| 4,780,300 A | | 10/1988 | Yokoyama et al. |
| 4,886,651 A | * | 12/1989 | Patel et al. .................. 423/359 |
| 5,180,570 A | * | 1/1993 | Lee et al. .................... 423/359 |
| 5,252,609 A | * | 10/1993 | Pinto .......................... 423/359 |
| 5,653,774 A | | 8/1997 | Bhattacharyya et al. |
| 5,741,474 A | * | 4/1998 | Isomura et al. .......... 423/648.1 |
| 6,106,793 A | * | 8/2000 | Badano et al. .............. 423/359 |
| 6,171,574 B1 | | 1/2001 | Juda et al. |
| 6,214,314 B1 | * | 4/2001 | Abbott ........................ 423/650 |
| 6,333,014 B1 | * | 12/2001 | Filippi ......................... 423/359 |

* cited by examiner

Primary Examiner—Wayne A. Langel
(74) Attorney, Agent, or Firm—Daniel N. Lundeen; Lundeen & Dickinson, LLP

(57) ABSTRACT

The converting of an existing methanol plant to make hydrogen and optionally methanol is disclosed. The converted plant utilizes the steam reformer (10) to which (a) a hydrocarbon, e.g., natural gas, or a lower alkanol, e.g., methanol, and (b) steam (water) are fed. Syngas is formed in the reformer (10). All or part of the syngas is processed in a CO converter (21) and/or a separation unit (22 & 28) to separate out carbon dioxide (24), carbon monoxide (30) and hydrogen (32). In the first mode, the CO converter (21) is isolated and the separated carbon dioxide (24) is fed either to the existing methanol synthesis loop (12) for methanol synthesis, or back into the feed to the reformer (10) to enhance carbon monoxide formation in the syngas (18). In the second mode, a lower alkanol is fed to the reformer (10), and the methanol synthesis loop (12) is shutdown and isolated from the rest of the plant. Any remaining syngas (38) not fed to the carbon dioxide separator (22) can be converted to methanol in the existing methanol synthesis loop (12) along with carbon dioxide (24) from the separator (22) and/or imported carbon dioxide (25), and hydrogen (35) from the separator (28). In the second mode, the separated carbon monoxide (30) is preferably recycled to the reformer (10) and/or to the CO converter (21) to enhance hydrogen production.

48 Claims, 3 Drawing Sheets

BIMODAL HYDROGEN MANUFACTURE

FIELD OF THE INVENTION

The present invention is directed generally to a process for making hydrogen by steam reforming a lower alkanol, e.g., methanol, and more particularly to a bimodally operable plant wherein in a first mode of operation the plant manufactures hydrogen and methanol by initially steam reforming a hydrocarbon feed, and in a second mode of operation the plant manufactures hydrogen by steam reforming a hydrocarbon or lower alkanol feed.

BACKGROUND OF THE INVENTION

The manufacture of hydrogen from methanol using a methanol reforming catalyst alone or in conjunction with a hydrogen-generating shift reactor is known in the art. Representative references disclosing this and similar processes include U.S. Pat. No. 4,175,115 to Ball et al (Ball); U.S. Pat. No. 4,316,880 to Jockel et al (Jockel); U.S. Pat. No. 4,780,300 to Yokoyama et al (Yokoyama) and U.S. Pat. No. 6,171,574 B1 to Juda et al (Juda), each of which is hereby incorporated herein by reference.

Ball discloses the production of synthesis gas by contacting methanol in the vapor phase with a catalyst that is a supported Group VIII metal. The metal may be used alone or in combination with one or more other metals from Groups I to VIII, excluding binary combinations of copper and nickel. Anhydrous methanol is preferably used since the presence of water makes the efficient production of a carbon monoxide and hydrogen mixture much more difficult. On the other hand, the methanol may be diluted with carbon monoxide, carbon dioxide or hydrogen. The feed may be diluted with recycle of carbon monoxide and hydrogen.

Jockel discloses a process for producing carbon monoxide and hydrogen by contacting methanol vapor with an indirectly heated zinc containing catalyst. The carbon monoxide is separated from the hydrogen by using adsorbers containing zeolite-type molecular sieves that allow the hydrogen to permeate through and sorbs the carbon monoxide. Water is minimized in the methanol to not in excess of 20 percent by weight to minimize the carbon dioxide content in the effluent.

Yokoyama discloses a process for reforming methanol by cracking 100 moles of methanol in admixture with 1 to 99 moles of water, thereby obtaining a gas containing hydrogen and carbon monoxide. Therefore, less than stoichiometric quantities of water are used. The process is preferably carried out using a catalyst that consists of a carrier comprising copper and chromium oxides with or without magnesium oxide and/or barium oxide and a catalytic component of nickel oxide or a mixture of nickel oxide and a basic oxide.

Juda discloses catalytic steam reforming of methanol and similar fuels to generate hydrogen. The hydrogen is purified by its permeation through a selective membrane. These two processes are linked by bounding a longitudinal tortuous flow path of a methanol reformate by a thin palladium-bearing membrane. The methanol reformate contains hydrogen, oxides of carbon, steam and methanol. The flow path contains a turbulence inducing material, in one case the methanol reforming catalyst crushed to a uniform sieve size.

The manufacture of hydrogen from a hydrocarbon, e.g., natural gas, using a hydrocarbon reforming catalyst is also known in the art. Representative references disclosing this and similar processes include U.S. Pat. Nos. 5,653,774 to Bhattacharyya et al (Bhattacharyya); 5,855,815 to Park et al (Park); 6,048,508 to Dummersdorf et al (Dummersdorf);

Bhattacharyya discloses a nickel containing reforming catalyst and a process using same wherein a hydrocarbyl compound, e.g. natural gas, is reformed using an oxygen-containing compound, e.g., molecular oxygen or carbon dioxide. Steam may be added when carbon dioxide is used to reduce coking of the catalyst so that deactivation does not occur. The amount of water as steam is preferably about 10 to 50 percent of the feed gases.

Park discloses a process for producing synthesis gas containing carbon monoxide and hydrogen from the reduction of carbon dioxide with natural gas or a lower hydrocarbon having methane as the main component and oxygen and steam over a catalyst. The catalyst is composed of nickel and, as promoters, alkali metal and alkaline earth metal component supported on silicon-containing support. The support has a high surface area and may be a zeolite, silica, silicate or silica-alumina which are stable under the reaction conditions disclosed therein. The objective of the process is to produce a synthesis gas having a low ratio of hydrogen to carbon monoxide from carbon dioxide and hydrocarbon by using inexpensive Ni catalyst.

Dummersdorf discloses a process for simultaneously obtaining pure carbon monoxide and pure hydrogen in a steam reformer plant for hydrogen or ammonia generation. Natural gas is fed to the steam reformer plant that has a primary reformer, a secondary reformer and down stream thereof, a CO conversion stage. A portion of the syngas stream discharged from the second reformer is treated to remove the carbon monoxide and a major portion of the steam contained therein to produce a pure CO stream. The thus treated syngas stream is combined with the remaining portion of the syngas stream discharged from the second reformer prior to entering the CO conversion stage, which is a hydrogen-generating shift reactor, wherein the carbon monoxide and water are converted into carbon dioxide and hydrogen.

The primary raw materials for methanol manufacture are, of course, carbon monoxide and hydrogen. In the typical methanol plant, natural gas or another hydrocarbon is reformed with steam and/or carbon dioxide to generate a syngas containing carbon dioxide, carbon monoxide and hydrogen. The syngas is supplied to a methanol synthesis unit to convert the carbon dioxide and hydrogen therein into methanol.

Market conditions, from time to time in various localities, can result in relatively low methanol prices (an oversupply) and/or high natural gas prices (a shortage) that can make methanol manufacture unprofitable. Operators of existing methanol manufacturing facilities can be faced with the decision of whether or not to continue the unprofitable manufacture of methanol in the hope that product prices will eventually rebound and/or raw material prices will drop to profitable levels. The present invention addresses a way of modifying an existing unprofitable methanol plant to make it more profitable when methanol prices are low and/or natural gas prices are high. The present invention also addresses a way of building a new plant with two modes of operation—one with a hydrocarbon feed and the other with an imported methanol feed.

As far as applicant is aware, there is no disclosure in the prior art for modifying existing methanol plants, including methanol/ammonia plants, to switch from methanol production in one mode to producing hydrogen in another mode when hydrogen becomes a more valuable product than methanol. Further, as far as applicant is aware, there is no disclosure in the prior art for modifying existing methanol plants, particularly the steam reformers thereof to reform either a hydrocarbon or a lower alkanol, e.g. methanol, using a hydrocarbon reforming catalyst with the optional presence of carbon dioxide, carbon monoxide, steam or a combination thereof.

SUMMARY OF THE INVENTION

The present invention involves the discovery that the large capital costs associated with hydrogen generation in a new hydrogen plant can be significantly reduced or largely eliminated by converting an existing methanol or methanol/ammonia plant to make hydrogen and/or ammonia. The present invention is equally applicable to a new plant wherein the syngas producing portion of the plant accepts either a hydrocarbon feed, e.g., natural gas, or a lower alkanol feed, preferably a $C_1$–$C_3$ alkanol feed, e.g., a methanol feed. The steam reformer is built or modified to accept either a natural gas feed or an imported methanol feed and to optionally have one or more additional feeds of carbon dioxide, carbon monoxide, steam or various combinations thereof. Depending on the mode of operation, the reformation takes place in the presence of a hydrocarbon and/or methanol reformation catalyst. Further, all or part of the syngas can be diverted from the methanol synthesis loop and supplied instead to a separator unit to recover $CO_2$, CO and hydrogen. When the steam reformer is operated with a lower alkanol feed, the methanol synthesis loop is shut down and isolated from the rest of the plant. In this case, all of the synthesis gas will be diverted from the methanol synthesis loop to the separation unit. When methanol and hydrogen are produced, the recovered $CO_2$ can be supplied to the reformer to enhance CO production, or to the methanol synthesis loop to make methanol. When hydrogen and not methanol is produced, the recovered CO can be supplied to the reformer to enhance hydrogen production, or to an optional CO converter that reacts CO and water (steam) to produce $CO_2$ and hydrogen. The recovered hydrogen can be supplied to the methanol synthesis loop (when in use) for methanol production, used for the manufacture of ammonia or other products, burned as a fuel, or exported, since the hydrogen is normally produced in excess of the requirements for methanol synthesis in the present invention.

The carbon dioxide and/or carbon monoxide can be fed into a steam reformer to which (1) natural gas or methanol and (2) optionally steam (water) are fed. Syngas is formed in the reformer wherein both (1) the natural gas or methanol and (2) the carbon dioxide and/or carbon monoxide are reformed to produce syngas. When reforming with carbon dioxide, the syngas has a minor proportion of carbon monoxide relative to reforming without added carbon dioxide. The $CO_2$ can be supplied to the methanol synthesis loop (when in operation), with additional CO from the synthesis gas and/or additional imported $CO_2$, for catalytic reaction with hydrogen to make methanol. When reforming with carbon monoxide, the goal is to reduce carbon monoxide formation and increase hydrogen formation by increasing carbon monoxide concentration using the recycled CO stream to establish reaction conditions unfavorable to additional CO production. Alternatively, when enhanced hydrogen production is desired, a CO converter may be employed. In this situation, the carbon dioxide is recycled to the reformer and the CO in the syngas plus optionally recycled CO are converted by reaction with steam in the CO converter to hydrogen and carbon dioxide using the shift reaction.

In the mode when the methanol synthesis loop is in operation, natural gas is preferably used as the hydrocarbon feed to the steam reformer containing a hydrocarbon steam reforming catalyst. The syngas can be split into a first part and a second part. The first syngas part is converted to methanol in a conventional methanol synthesis loop that is operated at less than design capacity of the original plant since less syngas is supplied to it. The second syngas part can be processed to separate out carbon dioxide and carbon monoxide, and the separated carbon dioxide can be fed back into the feed to the reformer to enhance carbon monoxide formation, and/or fed to the methanol synthesis loop to make methanol. The separated carbon monoxide can then be reacted with the methanol to produce acetic acid or an acetic acid precursor by a conventional process.

In the mode wherein the methanol synthesis loop is shut down and isolated from the rest of the plant, an imported lower alkanol, e.g., methanol, or hydrocarbon is used as a feed to the steam reformer. The steam reformer contains either a hydrocarbon steam reforming catalyst or a methanol steam reforming catalyst. The syngas is processed to separate out carbon dioxide and carbon monoxide, and the separated carbon monoxide may be recycled to the reformer to enhance carbon dioxide formation and/or reduce carbon monoxide formation. Alternatively, at least a portion of the syngas stream is diverted to an optional CO converter (also referred to as a hydrogen-generating shift reactor), wherein the carbon monoxide and water (steam) are reacted to produce hydrogen and carbon dioxide. Alternatively or additionally, the separated carbon monoxide can then be reacted with steam in the same or an additional optional CO converter to produce carbon dioxide and hydrogen. This carbon dioxide may similarly or additionally be recycled to the steam reformer. Alternatively, the carbon monoxide may be used as a feed to an acetic acid plant where the carbon monoxide is reacted with methanol to make acetic acid or an acetic acid precursor by a conventional process.

In the mode wherein natural gas is used as a feed to the steam reformer, one embodiment of the method comprises the steps of: (a) diverting a portion of the syngas stream from at least one steam reformer to a separation unit; (b) operating the methanol synthesis loop with a feed comprising the remaining syngas stream to produce less methanol than the original methanol plant; (c) operating the separation unit to separate the diverted syngas into at least a carbon monoxide-rich stream and a hydrogen-rich stream, preferably wherein the quantity of hydrogen in the hydrogen-rich stream is greater than any net hydrogen production of the original methanol plant; and (d) reacting the hydrogen-rich stream from the separation unit with nitrogen from a nitrogen source to form ammonia, wherein the diversion of the syngas stream is balanced for the approximately stoichiometric production of the methanol in the methanol synthesis loop and ammonia in the ammonia reactor.

In the mode wherein a lower alkanol, preferably methanol, is used as feed to the steam reformer, the method comprises the steps of: (a) feeding the syngas stream from at least one steam reformer to a separation unit; (b) isolating the methanol synthesis loop from the remainder of the plant; (c) operating the separation unit to separate the syngas into at least a carbon monoxide-rich stream and a hydrogen-rich stream; and (d) reacting the hydrogen-rich stream from the separation unit with the nitrogen from a nitrogen source to form ammonia.

Preferably, at least one steam reformer is built or modified to increase carbon monoxide production in the syngas stream in the first mode of operation. The steam reformer contains a hydrocarbon reformation catalyst and is used to reform a hydrocarbon, e.g., natural gas, or a lower alkanol ($C_1$–$C_3$ alcohol), e.g., methanol, to syngas. Alternatively, the steam reformer may utilize a methanol reformation catalyst to generate syngas when the plant is operating in the second mode with a methanol feed. The steam reformer is preferably modified to operate at a higher temperature in the first mode to enhance carbon monoxide production.

The methanol and carbon monoxide can be reacted to form acetic acid in a direct catalytic reaction as in the Mosanto-BP process, for example, or alternatively can comprise the intermediate formation of methyl formate and isomerization of the methyl formate to acetic acid, the intermediate reaction of a mole of CO and two moles of methyl alcohol to form methyl acetate and hydrolysis of the methyl acetate to acetic acid and methanol, or the carbonylation of the methyl acetate to form acetic anhydride.

Separated hydrogen, which is generally produced in excess beyond that required for methanol synthesis in the present process, can also be reacted with nitrogen, in a conventional manner, to produce ammonia. Also, a portion of acetic acid that is produced can be reacted in a conventional manner with oxygen and ethylene to form vinyl acetate monomer. The nitrogen for the ammonia process (especially for any added ammonia capacity in a retrofit of an original methanol plant comprising an ammonia synthesis loop) and the oxygen for the vinyl acetate monomer process, can be obtained from a conventional air separation unit.

Broadly, the present invention provides, in one aspect, a process for making hydrogen, comprising reforming a lower alkanol in the presence of excess steam and a hydrocarbon reforming catalyst at a temperature of at least 600° C., optionally with shift conversion, to form a hydrogen-containing gas, and recovering hydrogen therefrom. The process may further comprise recovery of carbon monoxide from the hydrogen-containing gas and recycle thereof upstream from the shift converter (also referred to as a CO converter).

Broadly, the present invention provides, in another aspect, a method converting an original methanol plant to a converted plant having bimodal operation, the method comprising the steps of: (a) providing the original methanol plant; (b) providing for selectively supplying a gaseous feed to the at least one steam reformer, wherein in a first mode the gaseous feed is a hydrocarbon and in a second mode the gaseous feed is a vaporized lower alkanol; (c) installing a vaporizer for vaporizing a lower alkanol from an imported source into the vaporized lower alkanol; (e) loading the at least one steam reformer with a hydrocarbon or methanol reformation catalyst for syngas generation; (f) installing a separation unit for separating a stream containing carbon dioxide, carbon monoxide and hydrogen into respective streams rich in carbon dioxide, carbon monoxide and hydrogen; (g) providing for diverting all or part of the syngas stream originally fed to the methanol synthesis loop to the separation unit; (h) providing for optionally, selectively supplying to the at least one steam reformer in the first mode at least a portion of the carbon dioxide-rich stream and in the second mode at least a portion of the carbon monoxide-rich stream; (i) providing for optionally supplying in the first mode at least another portion of the carbon dioxide-rich stream to the methanol synthesis loop; and (j) installing isolation valves for isolating the methanol synthesis loop from the remainder of the converted plant when operated in the second mode. The original methanol plant comprises (i.e., has at least the following) (1) at least one steam reformer for converting a hydrocarbon to a syngas stream containing hydrogen, carbon monoxide, and carbon dioxide, and (2) a methanol synthesis loop for converting hydrogen and carbon monoxide from the syngas stream to methanol. If the original methanol plant has an ammonia reactor, the method further comprises providing for supplying at least a portion of the hydrogen-rich stream from the separation unit to the ammonia reactor. Otherwise, the method may further comprise installing an ammonia reactor for reacting hydrogen and nitrogen to form ammonia; providing for supplying at least a portion of the hydrogen-rich stream from the separation unit to the ammonia reactor; and providing a source of nitrogen to the ammonia reactor.

The method may further comprise installing a CO converter for reacting carbon monoxide and steam to form a shift gas having at least hydrogen and carbon monoxide; providing for supplying at least a portion of the syngas from the at least one steam reformer to the CO converter, wherein the syngas has carbon monoxide and steam; and installing isolation valves for isolating the CO converter from the remainder of the converted plant when the methanol synthesis loop is in use in the first mode. In one embodiment, this method may further comprise providing for supplying all the syngas to the CO converter; and providing for supplying the shift gas instead of the syngas to the separation unit. The plant may be further modified to optionally supply steam to the CO converter. At least a portion of the carbon monoxide-rich stream may be recycled to the CO converter.

In this method, the separation unit may comprise a solvent absorber and stripper for carbon dioxide recovery and a cryogenic distillation unit for carbon monoxide and hydrogen recovery. Further, the steam reformer may be modified for high temperature use.

The method for operating this converted plant comprises the steps of: (1) selecting between the first mode and the second mode of operation; and (2) operating the converted plant in the selected mode. The first mode of operation has at least the following steps (1) feeding the hydrocarbon to the at least one steam reformer containing the hydrocarbon reforming catalyst, (2) operating the at least one steam reformer to generate syngas, (3) separating at least a portion of the syngas stream in the separation unit into respective streams rich in carbon dioxide, carbon monoxide and hydrogen, and (4) operating the methanol synthesis loop with a feed comprising (i) carbon dioxide and (ii) hydrogen to produce methanol. The second mode of operation has at least the following steps: (1) vaporizing the lower alkanol, (2) feeding the vaporized lower alkanol to the at least one steam reformer, (3) operating the at least one steam reformer to generate syngas, and (4) separating all or part of the syngas stream in the separation unit into respective streams rich in carbon dioxide, carbon monoxide and hydrogen, and (5) isolating the methanol synthesis loop from the remainder of the converted plant.

When the first mode is selected, the feed to the methanol synthesis loop can include imported carbon dioxide and/or a portion of the synthesis gas. Preferably, essentially all of the syngas stream is supplied to the separation step. The hydrogen supplied to the methanol synthesis loop is preferably provided by supplying at least a portion of the hydrogen-rich stream to the methanol synthesis loop. The amount of the hydrogen-rich stream is generally in excess of the stoichiometric hydrogen required by the methanol synthesis loop. Preferably, essentially all of the carbon dioxide-rich stream is supplied to the synthesis loop.

In the first mode, the at least one steam reformer preferably has a second feed comprising a carbon dioxide-rich stream. This may be an imported stream or recycled from the separation unit. The carbon dioxide is converted to carbon monoxide in the reformer. The carbon dioxide-rich stream may be a mixed CO/carbon dioxide stream, for example, in a 1:2 to 2:1 molar ratio.

An imported carbon dioxide-rich stream can be supplied to the methanol synthesis loop (only in the first mode) or to the separation unit, but as noted above is preferably supplied to the reformer for conversion of the carbon dioxide to CO (only in the first mode).

In either mode, steam is preferably fed to the at least one steam reformer to avoid coke formation. The amount of steam added is preferably in excess of stoichiometeric for reforming the hydrocarbon or lower alkanol feed.

In a preferred embodiment wherein the first mode is selected, the method for operating the modified or retrofitted plant comprises (1) supplying a major portion of the syngas stream to the separation unit for separating the syngas stream into respective streams rich in carbon dioxide, carbon monoxide and hydrogen, and (2) operating the methanol synthesis loop with a feed comprising the carbon dioxide-rich stream from the separation unit, a minor portion of the syngas stream, and an additional source of carbon dioxide to produce a methanol stream.

In another preferred embodiment wherein the first mode is selected, the method for operating the converted plant comprises (1) supplying all of the syngas stream to a separation unit for separating the syngas stream into respective streams rich in carbon dioxide, carbon monoxide and hydrogen, and (2) operating the methanol synthesis loop with a feed comprising the carbon-dioxide-rich stream from the separation unit, a portion of the hydrogen-rich stream from the separation unit, a minor portion of the syngas stream, and carbon dioxide from an additional source, to produce a methanol stream.

In another aspect, the present invention provides a process for making hydrogen and optionally methanol. The process comprising the steps of: (1) selecting between a first mode of operation where hydrogen and methanol are produced and a second mode of operation where hydrogen and not methanol is produced; (2) reforming a hydrocarbon in a first mode or a lower alkanol in a second mode with steam using a reformation catalyst to form a syngas containing hydrogen, carbon monoxide, and carbon dioxide, (3) recovering heat from the syngas to form a cooled syngas stream; and (4) compressing the cooled syngas stream to a separation pressure. In the first mode, methanol is produced by operating a methanol synthesis loop to react hydrogen with carbon dioxide. In the second mode, the methanol synthesis loop is isolated from the remainder of the process. In the first mode, the reforming step is conducted to enhance the production of carbon monoxide and hydrogen and the reformation catalyst is a hydrocarbon reformation catalyst. In the second mode, the reforming step is conducted to enhance hydrogen production and the reformation catalyst is selected from the group consisting of hydrocarbon reformation catalyst, methanol reformation catalyst and a combination thereof.

In one embodiment when the first mode is selected, the process further comprises separating at least a portion of the compressed syngas in a separation unit into a carbon dioxide-rich stream, a carbon monoxide-rich and a hydrogen-rich stream. Further, the sources of the hydrogen and carbon dioxide to the methanol synthesis loop are a first portion of the hydrogen from the separation unit and the carbon dioxide from the separation unit. Additional carbon dioxide from another source may also be fed to the methanol synthesis loop.

In another embodiment when the first mode is selected, the reforming step is conducted in the presence of carbon dioxide and the syngas produced by the reforming step has a molar R ratio (($H_2-CO_2$)/($CO+CO_2$)) from about 2.0 to about 2.9. The carbon dioxide present in the reforming step is preferably obtained by recycling the carbon dioxide-rich stream to the reforming step.

With the process in the first mode, the method may further include the steps of diverting a major portion of the compressed syngas to a separation unit; separating the syngas diverted to the separation unit into a carbon dioxide-rich stream, a carbon monoxide-rich stream and a hydrogen-rich stream; further compressing the remaining minor portion of the syngas to a methanol synthesis pressure higher than the separation pressure; and operating a methanol synthesis loop to convert the hydrogen, carbon monoxide and carbon dioxide in the further compressed syngas into a methanol stream.

The process preferably has a molar ratio of carbon dioxide to hydrocarbon comprising natural gas or methanol in feed to the reforming step from about 0.1 to 0.5. This feed preferably has a ratio of steam to natural gas or methanol from about 2 to 6. The methanol synthesis loop can be operated substantially below a total maximum combined design throughput of all methanol synthesis reactor(s) in the loop.

In the second mode, the reforming step is conducted to enhance the hydrogen content of the syngas. This step is preferably conducted in the presence of steam and optionally carbon monoxide fed thereto. The process may further comprise separating the syngas in the separation unit into a carbon dioxide-rich stream, a carbon monoxide-rich stream and a hydrogen-rich stream. The carbon monoxide used in the reforming step is preferably obtained by recycling the carbon monoxide-rich stream to the reforming step.

In another embodiment, the process further comprises reacting the carbon monoxide in the syngas with steam in a shift reaction to form a shift gas having at least carbon dioxide and hydrogen. All or part of the syngas from the reformer may be supplied to the CO converter prior to entering the separation unit. If not in use, the CO converter may be isolated from the remainder of the converted plant. The shift gas is preferably separated into a carbon dioxide-rich stream and a hydrogen-rich stream. The carbon monoxide-rich stream from the separation unit is preferably recycled at least in part to the steam reformer to reduce carbon monoxide production in the steam reformer.

The process can further comprise the step of reacting the hydrogen in the hydrogen-rich stream with nitrogen in an ammonia synthesis reactor to make ammonia. The process can also comprise the step of separating air into a nitrogen stream and an oxygen stream and supplying the nitrogen stream to the ammonia synthesis reactor.

In another embodiment, the present invention provides a method for converting an original methanol plant into a converted plant for manufacturing hydrogen and optionally methanol. The original methanol plant comprises (1) at least one steam reformer for converting a hydrocarbon to a syngas stream containing hydrogen, carbon monoxide, and carbon dioxide, and (2) a methanol synthesis loop for converting hydrogen and carbon monoxide from the syngas stream to methanol. The method comprises (a) providing the original methanol plant; (2) providing for supplying a gaseous feed to the at least one steam reformer, wherein the gaseous feed is a vaporized lower alkanol; (3) installing a vaporizer for vaporizing a lower alkanol from an imported source into the vaporized lower alkanol; (4) loading the at least one steam reformer with a reformation catalyst for syngas generation selected from hydrocarbon reformation catalyst, methanol reformation catalyst and a combination thereof; (5) installing a separation unit for separating all or part of the syngas stream into respective streams rich in carbon dioxide, carbon monoxide and hydrogen; (6) providing for diverting all of the syngas stream originally fed to the methanol synthesis loop to the separation unit; (7) providing for supplying at least a portion of the carbon monoxide-rich stream to the at least one steam reformer; (8) installing isolation valves for isolating the methanol synthesis loop from the remainder of the converted plant; (9) installing an ammonia reactor for reacting hydrogen and nitrogen to form ammonia; (10) providing for supplying at least a portion of the hydrogen-rich stream from the separation unit to the ammonia reactor; and (11) providing for supplying nitrogen to the ammonia reactor.

Also provided is a method of operating the foregoing converted plant. This method comprises (1) vaporizing the lower alkanol, (2) feeding the vaporized lower alkanol to the at least one steam reformer, (3) operating the at least one steam reformer to generate syngas wherein hydrogen production is enhanced; (4) separating all or part of the syngas stream in the separation unit into respective streams rich in carbon dioxide, carbon monoxide and hydrogen, (5) isolating the methanol synthesis loop from the remainder of the converted plant, (6) providing a source of nitrogen, and (7) reacting at least a portion of the hydrogen-rich stream from the separation unit with nitrogen. The lower alkanol is preferably methanol. The reformation catalyst is preferably a hydrocarbon reformation catalyst.

The modified steam reformer is preferably modified to operate at a higher temperature to enhance the carbon conversion to carbon monoxide. The separation unit can include a solvent absorber and stripper for carbon dioxide recovery, and a cryogenic distillation unit for carbon monoxide and hydrogen recovery.

The compression unit preferably has a three-stage compressor, and the syngas stream diversion preferably occurs between the second and third compression stages. The third compressor stage is preferably modified for operation at a lower throughput than the original methanol plant. Where the methanol synthesis loop of the original methanol plant includes a recycle loop compressor, the recycle loop compressor can also be modified for operation at a lower throughput.

The method can also comprise importing a stream of mixed CO/carbon dioxide, for example in a 1:2 to 2:1 molar ratio. The imported mixed CO/carbon dioxide stream can be supplied to the methanol synthesis loop or to the separation unit, but is preferably supplied to the reformer where the carbon dioxide therein is substantially converted to CO.

The method can further comprise the step of reacting the hydrogen in the hydrogen-rich stream with nitrogen to make ammonia. Where the original methanol plant produces a hydrogen-rich stream comprising a loop purge from the methanol synthesis loop that was reacted with nitrogen to make ammonia, the retrofitted plant can use the hydrogen-rich stream from the separation unit as a primary hydrogen source for the ammonia production. With the additional hydrogen available from the syngas, additional ammonia can be produced in the retrofitted plant relative to the original methanol plant.

The method can further comprise installing a vinyl acetate synthesis reactor for reacting a portion of the acetic acid with ethylene and oxygen to make vinyl acetate monomer. An air separation unit can be installed to make the oxygen for the vinyl acetate monomer unit, and the nitrogen produced from the air separation unit preferably matches the nitrogen required for the additional ammonia production.

DETAILED DESCRIPTION OF THE INVENTION

Figure 1:
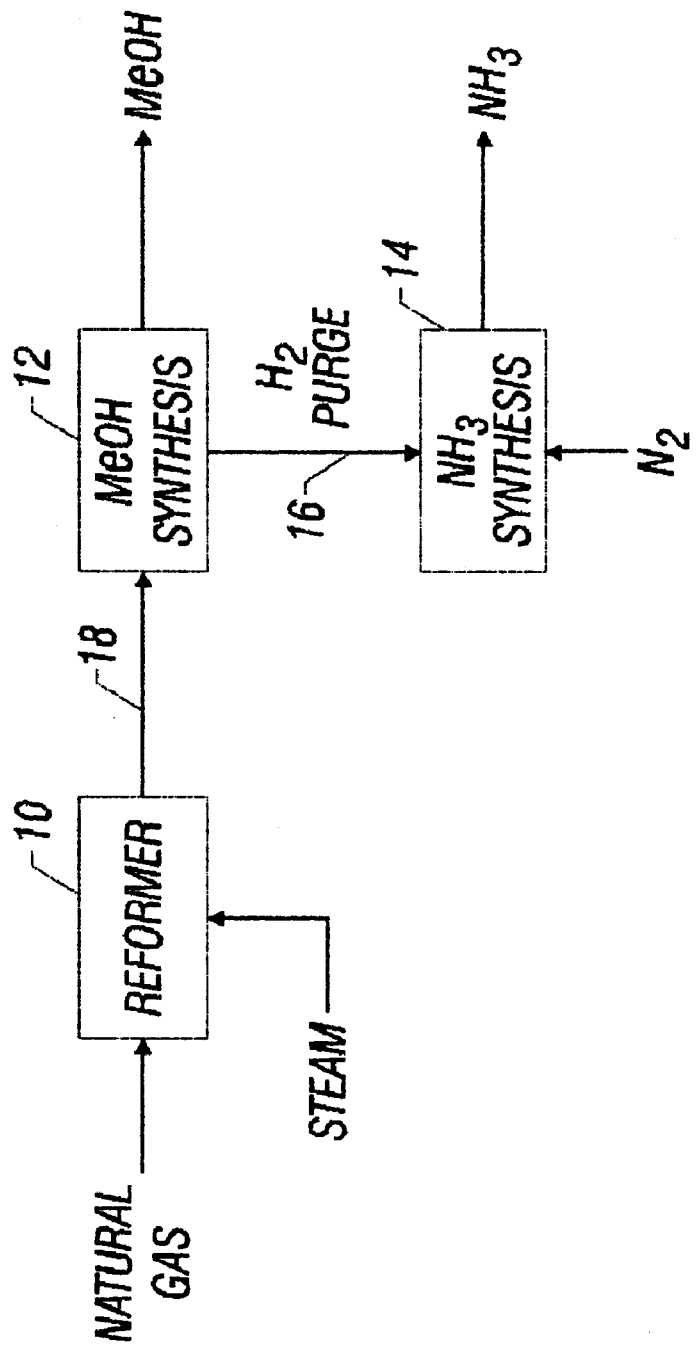
FIG. 1 (prior art) is an overall block flow diagram of a typical methanol/ammonia plant using hydrogen from the methanol synthesis loop purge to make ammonia.

With reference to FIG. 1, an original plant which can be converted according to one embodiment of the present invention has an existing conventional steam reformer unit 10, methanol (MeOH) synthesis unit 12 and preferably ammonia synthesis unit 14 wherein hydrogen for the ammonia synthesis unit 14 is taken as purge stream 16 from the methanol synthesis loop. The retrofit of the present invention is generally applicable to any plant that generates and uses synthesis gas to make methanol. As used in the present specification and claims, reference to "original plant" shall mean the plant as built and including any intervening modifications prior to the retrofit of the present invention.

The reformer unit 10 is typically a fired furnace containing parallel tube banks filled with conventional reforming catalyst such as alumina-supported nickel oxide, for example. The feed to the reformer(s) is any conventional reformer feed such as a lower hydrocarbon, typically naphtha or natural gas. The reformer can be a single-pass reformer or a two-stage reformer, or any other commercially available reformer, such as, for example, a KRES unit available from Kellogg, Brown & Root, as is known to those skilled in the art. The reformer effluent of the original methanol plant can contain any conventional $H_2$:CO ratio, but is normally close to 2.0 in plants making solely methanol, and substantially higher, e.g. 3.0 and above, in plants producing a separate hydrogen product or intermediate hydrogen-containing stream, e.g. for ammonia synthesis. The hydrogen-containing stream is typically obtained as purge stream 16 from the methanol synthesis unit 12 loop which is necessary to keep the level of hydrogen and inerts from building up in the synthesis gas recirculated through the methanol synthesis unit 12.

Figure 2:
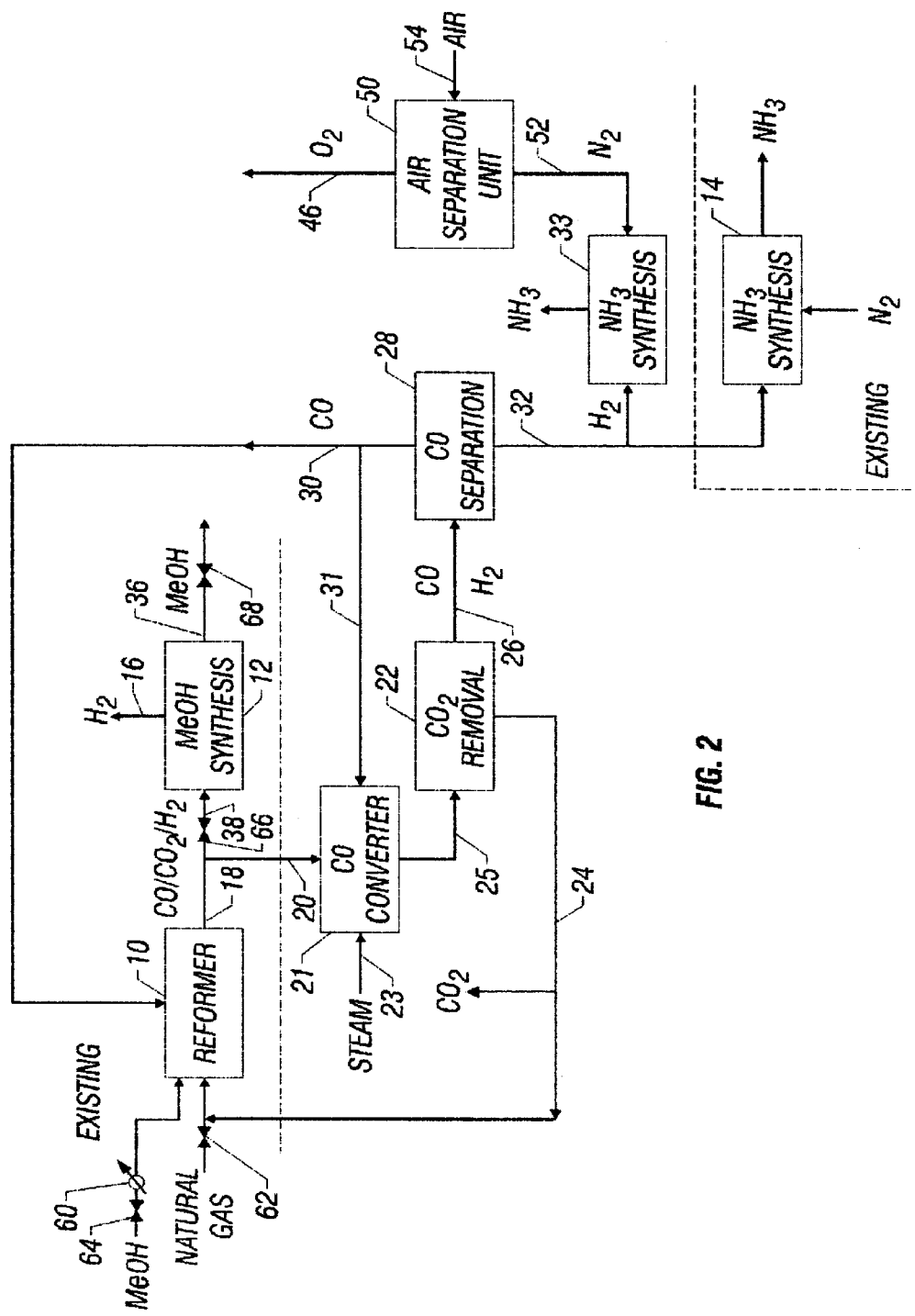
FIG. 2 is an overall block flow diagram of the plant of FIG. 1 after it has been converted according to the present invention to make additional hydrogen and ammonia, plus allow for reforming either natural gas or methanol, and wherein the CO from the separation unit can be supplied to either or both the reformer and CO converter, which reacts CO with steam to make hydrogen and carbon dioxide.

According to the present invention, the original plant of FIG. 1 is converted to produce hydrogen, ammonia, and optionally methanol using the existing reformer 10 and methanol synthesis unit 12, and keeping any ammonia synthesis unit 14, as shown in FIG. 2. The reformer 10 is fed either in the first mode a hydrocarbon feed, e.g., natural gas, or in the second mode a lower alkanol feed, e.g., methanol. A methanol feed would be used over natural gas when economics dictate. Valves 62 and 64 control which feed is used. The methanol is preferably vaporized in vaporizer 60 prior to being fed to reformer 10. Thus, the retrofitted plant in FIG. 2 can operate in a first mode using a natural gas feed or in a second mode using a methanol feed. In the second mode, the methanol synthesis unit 12 is shut down and isolated from the remainder of the plant using isolation valves 66 and 68.

Depending in which mode the plant is operating, all or a portion of the effluent 18 from the reformer 10 is diverted from the methanol synthesis unit 12 via line 20 to an optional new CO converter 21 and a new $CO_2$ removal unit 22. The CO converter 21 reacts CO in the stream from line 20 with steam in line 20 and/or steam from line 23 into carbon dioxide and hydrogen. The CO converter 21 may have two stages, a high temperature stage and a low temperature stage (not shown). The $CO_2$ removal unit 22 separates the stream from line 25 into a $CO_2$-rich stream 24 and a $CO_2$-lean stream 26 using conventional $CO_2$ separation equipment and methodology such as, for example, absorption-stripping with a solvent such as water, methanol, generally aqueous alkanolamines such as ethanolamine, diethanolamine, methyldiethanolamine and the like, aqueous alkali carbonates such as sodium and potassium carbonates, and the like. Such $CO_2$ absorption-stripping processes are commercially available under the trade designations Girbotol, Sulfinol, Rectisol, Purisol, Fluor, BASF (aMDEA) and the like.

In the first mode of operation (i.e., hydrocarbon feed to reformer 10), the $CO_2$ recovered from the $CO_2$ removal unit 22 or from another source can be supplied to the reformer 10 (see FIG. 2) and/or to the methanol synthesis unit 12 (this option not shown). Increasing the $CO_2$ in the feed to the reformer 10 increases the CO content of the effluent 18. Analogous to steam reforming where a hydrocarbon reacts with steam to form synthesis gas, the reaction of the hydrocarbon with carbon dioxide is often called $CO_2$ reforming. As the carbon dioxide content of the reformer feed is increased, the share of the carbon in the carbon monoxide in the product synthesis gas 18 that is supplied from the carbon dioxide increases in relative proportion and the share originating from the hydrocarbon or lower alkanol decreases. So, for a given CO production rate, the hydrocarbon feed gas requirement is reduced. During the early stage of reforming, heavier hydrocarbons are converted to methane:

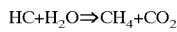

The main steam and $CO_2$ reforming reactions convert methane or methanol to hydrogen and carbon monoxide. The conversion of the heavier hydrocarbons goes to completion. For methane, the reforming reactions are:

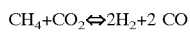

In the second mode of operation (i.e., lower alkanol, e.g., methane, fed to reformer 10), the presence of steam reduces CO production in favor of carbon dioxide formation as seen in the following reforming reactions:

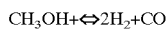

Thus, an excess of steam minimizes the probability of carbon monoxide being formed during the reforming of methanol. Excess steam has the added benefit of minimizing coke formation, which deactivates the catalyst. Further, by recycling carbon monoxide to the reforming reaction site via line 30 to the reformer 10, conditions become less favorable to CO production. The shift reaction converts carbon monoxide to carbon dioxide and more hydrogen:

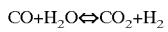

This reaction may occur in the steam reformer 10. To the extent that CO is produced and not converted in the steam reformer 10, the CO converter 21 utilizing the shift reaction may be incorporated into the process as shown in FIG. 2 to convert the CO remaining in line 20 and any CO recycled via line 31 into $CO_2$ and hydrogen. Alternatively, the CO converter 21 could be located to accept the stream from line 18, that is, all the syngas exiting the reformer 10 (this embodiment not shown). The steam reforming, $CO_2$ reforming, and shift reaction are equilibrium-restricted. The overall reaction is strongly endothermic.

For purposes of operating in the first mode, the reformer 10 can, if desired, be modified for additional heat input for supplemental $CO_2$ reforming and additional heat recovery. The effluent 18 from the modified reformer 10 has a molar ratio of hydrogen minus $CO_2$ to CO plus $CO_2$ (referred to in the present specification and claims as the "R ratio" ($H_2-CO_2$)/($CO+CO_2$)), which can be optimized for methanol synthesis, preferably within the range from 2.0 to 2.9. The possibility of optimizing the R ratio arises from the discovery that the hydrogen for the ammonia synthesis no longer needs to be obtained as the methanol purge stream 16, but can instead be recovered from the syngas diverted via line 20 as discussed in more detail below.

The $CO_2$-lean stream 26 contains primarily CO and hydrogen and can be separated in CO separation unit 28 into a CO-rich stream 30 and a hydrogen-rich stream 32. The separation unit 28 can comprise any equipment and/or methodologies for separating the CO/hydrogen mixture into relatively pure CO and hydrogen streams, such as, for example, semi-permeable membranes, cryogenic fractionation, or the like. Cryogenic fractional distillation is preferred, and can include simple partial condensation without any columns, partial condensation with columns, optionally with a pressure swing absorption (PSA) unit and a hydrogen recycle compressor, or methane wash. Normally, partial condensation with columns is sufficient for obtaining CO and hydrogen of sufficient purity for acetic acid and ammonia production, respectively, for example, keeping equipment and operating costs to a minimum, although the PSA unit and hydrogen recycle compressor can be added for increasing the hydrogen purity and CO production rate. For purposes of acetic acid manufacture, the CO stream 30 preferably contains less than 1000 ppm hydrogen and less than 2 mole percent nitrogen plus methane. For ammonia production, the hydrogen stream 32 which is sent to a nitrogen wash unit (not shown) preferably contains at least 80 mol % hydrogen, more preferably at least 95 mol % hydrogen.

A portion of the hydrogen stream 32 is supplied to the existing ammonia synthesis unit 14 in place of the methanol loop purge stream 16. The quantity of hydrogen produced in the stream 32 is generally much larger than the amount previously supplied via line 16. This is due in large part to the fact that less methanol is made in the retrofitted plant, and thus less hydrogen is consumed for methanol synthesis. The additional hydrogen capacity can be used as a fuel supply, or as a raw hydrogen source for another process, such as, for example, increased ammonia conversion. Additional ammonia can be made by supplying a portion of the additional hydrogen to the existing ammonia synthesis reactor 14 where the ammonia conversion capacity can be increased, and/or by installing additional ammonia synthesis unit 33. The increased ammonia capacity can be complemented by the presence of existing ammonia handling, storage and transport facilities that may be able to accommodate the additional ammonia capacity with little or no modification.

The methanol synthesis unit 12 is a conventional methanol conversion unit such as, for example, an ICI reactor. The methanol synthesis unit 12 of the retrofitted plant shown in FIG. 2 can be isolated from the remainder of the plant using valves 66 and 68 when the plant is operated in the second mode. The methanol synthesis unit 12 is used when the plant is operating in the first mode and is essentially the same as in the original plant prior to the retrofit, except that the quantity of methanol produced is substantially lower, preferably about half of that of the original plant. Concomitantly, the loop recycle compressor (not shown) is operated at a lower capacity and the purge stream 16 is considerably reduced in quantity. As mentioned above, the purge stream 16 is no longer needed for supplying the hydrogen to the ammonia converter 14, since this is now supplied in the converted plant from the hydrogen stream 32 separated directly from the portion of the reformer 10 effluent 18 diverted from the feed to the methanol synthesis unit 12 via line 20. If desired, the purge stream 16 can now be used for fuel and/or as a hydrogen source for hydrodesulfurization of the feed to the reformer 10. Since there is no longer any need to pass the excess hydrogen through the methanol synthesis unit 12 for use in the ammonia unit 14, the feed to the methanol synthesis unit 12, i.e. the effluent 18, can be compositionally optimized for more efficient methanol conversion, as described above. Although not shown in FIG. 2, additional hydrogen from line 32 if necessary may be fed to the methanol synthesis unit 12 from CO separator 28 in the first mode of operation. It may also be desirable to modify the methanol synthesis unit 12, if desired during the retrofit, to include any other modifications that are not present in the original plant, but have become conventional and have been developed for methanol synthesis loops since the construction of the original plant, and have not previously been incorporated therein.

When the plant is operated in the first mode, the amount of syngas in the effluent 18 from the reformer 10 that is diverted to $CO_2/CO/H_2$ separation is preferably balanced to provide a stoichiometric ratio of methanol and CO, for example, to produce acetic acid therefrom. Preferably, the ratio of CO in line 30 and methanol in line 36 is about equal or the methanol is produced at a 10–20% molar excess, e.g. a molar ratio from 1.0 to about 1.2. To produce this ratio of methanol and CO, a relatively larger quantity (total kg/hr) of the effluent 18 is diverted into line 20, and the remaining minor portion is fed in line 38 to the methanol synthesis unit 12.

A conventional (preferably cryogenic) air separation unit 50 is used to produce a nitrogen stream 52. There is also produced oxygen in line 46 available for export. The amount of air separated can be matched to produce the nitrogen required via line 52 for the additional ammonia capacity added by ammonia synthesis unit 33 as mentioned above.

Figure 3:
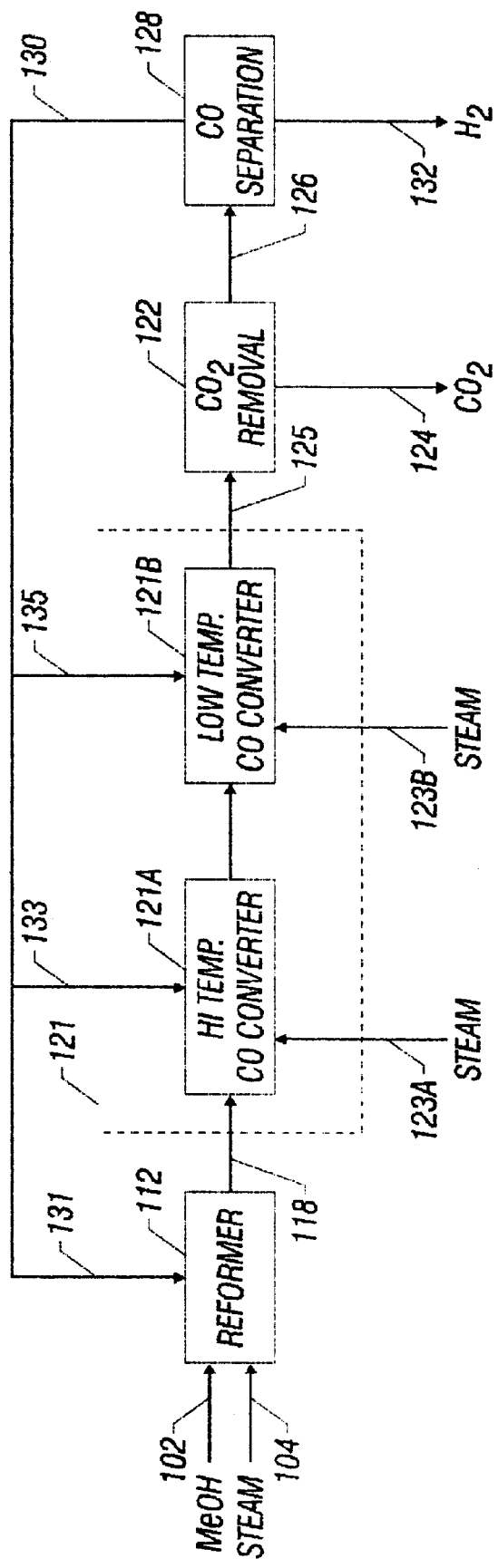
FIG. 3 is a schematic block diagram of a plant according to the present invention for steam reforming a lower alkanol to generate a syngas, optionally CO converting the CO in the syngas, and recovering the hydrogen therefrom.

Referring now to FIG. 3, a plant 100 is shown for reforming a lower alkanol, preferably methanol, to generate hydrogen. The plant 100 has a steam reformer 112, a CO converter 121, a $CO_2$ removal unit 122, and CO separation unit 128. The lower alkanol stream 102 and steam 104 are fed to the reformer 112 to generate syngas containing carbon dioxide, carbon monoxide, steam and hydrogen. The steam is preferably fed in excess of stoichiometric requirements for converting the lower alkanol, for example methanol, to hydrogen and carbon dioxide, preferably at least 2:1 molar ratio of steam:alkanol, more preferably at least 2,5:1, and yet more preferably at least 3:1, especially if the alkanol is other than methanol. The reformer 112 contains a reformation catalyst selected form the group consisting of hydrocarbon reformation catalysts, methanol reformation catalysts and a combination thereof. The reformer is operated a high temperature, preferably at least 600° C., more preferably at least 700° C., yet more preferably at least 800° C., and more preferably at least 1000° C.

The syngas is the fed via line 118 to the CO converter 121, in this case a two stage CO converter having a high temperature CO converter 121A and a low temperature CO converter 121 B, which is reacted with water (steam) to generate a shift gas containing more hydrogen and carbon dioxide than the syngas. Optionally, steam may be fed via lines 123A and/or 123B to the high temperature CO converter 121 A and/or the low temperature CO converter 121 B, respectively, if the steam contained in the syngas is stoichiometrically insufficient to convert the CO to hydrogen and carbon dioxide.

The shift gas in line 125 is then fed into the $CO_2$ removal unit 122 to generate a $CO_2$-rich stream 124 and a $CO_2$-lean stream 126. The $CO_2$-lean stream 126 is then fed to the CO separation unit 128 to generate a hydrogen-rich steam 132 as a product stream and a carbon monoxide-rich stream 130. The carbon monoxide-rich stream 130 may recycled via lines 131, 133 and 135 to the reformer 112, the high temperature CO converter 121A and/or the low temperature CO converter 121B, respectively, to enhance hydrogen production.

What is claimed is:

1. A method for converting an original methanol plant to a converted plant, the method comprising the steps of:

providing the original methanol plant having
at least one steam reformer for converting a hydrocarbon to a syngas stream containing hydrogen, carbon monoxide, and carbon dioxide, and
a methanol synthesis loop for converting hydrogen and carbon monoxide from the syngas stream to methanol;

providing for supplying a gaseous feed to the at least one steam reformer, wherein the gaseous feed is a vaporized lower alkanol;

installing a vaporizer for vaporizing a lower alkanol from an imported source into the vaporized lower alkanol;

loading the at least one steam reformer with a reformation catalyst for syngas generation selected from hydrocarbon reformation catalyst, methanol reformation catalyst and a combination thereof;

installing a separation unit for separating the syngas stream into respective streams rich in carbon dioxide, carbon monoxide and hydrogen;

providing for diverting the syngas stream originally fed to the methanol synthesis loop to the separation unit;

providing for supplying at least a portion of the carbon monoxide-rich stream to the at least one steam reformer upstream of an optional shift converter;

installing isolation valves for isolating the methanol synthesis loop from the remainder of the converted plant.

2. The method of claim 1 further comprising:

installing an ammonia reactor for reacting hydrogen and nitrogen to form ammonia;

providing for supplying at least a portion of the hydrogen-rich stream from the separation unit to the ammonia reactor; and providing for supplying nitrogen to the ammonia reactor.

3. A method for operating the converted plant of claim 2, the method comprising the steps of:
vaporizing the lower alkanol,
feeding the vaporized lower alkanol to the at least one steam reformer,
operating the at least one steam reformer to generate syngas wherein hydrogen production is enhanced,
separating all or part of the syngas stream in the separation unit into respective streams rich in carbon dioxide, carbon monoxide and hydrogen,
isolating the methanol synthesis loop from the remainder of the converted plant,
providing a source of nitrogen, and
reacting at least a portion of the hydrogen-rich stream from the separation unit with nitrogen.

4. A method for operating the converted plant of claim 1, the method comprising the steps of:
vaporizing the lower alkanol,
feeding the vaporized lower alkanol to the at least one steam reformer,
operating the at least one steam reformer to generate syngas wherein hydrogen production is enhanced,
separating all or part of the syngas stream in the separation unit into respective streams rich in carbon dioxide, carbon monoxide and hydrogen, and
isolating the methanol synthesis loop from the remainder of the converted plant.

5. The method of claim 1, wherein the lower alkanol is methanol.

6. The method of claim 1, wherein the reformation catalyst is a hydrocarbon reformation catalyst.

7. A method for converting an original methanol plant to a converted plant having bimodal operation, the method comprising the steps of:
providing the original methanol plant having
at least one steam reformer for converting a hydrocarbon to a syngas stream containing hydrogen, carbon monoxide, and carbon dioxide, and
a methanol synthesis loop for converting hydrogen and carbon monoxide from the syngas stream to methanol;
providing for selectively supplying a gaseous feed to the at least one steam reformer, wherein in a first mode the gaseous feed is a hydrocarbon and in a second mode the gaseous feed is a vaporized lower alkanol;
installing a vaporizer for vaporizing a lower alkanol from an imported source into the vaporized lower alkanol;
loading the at least one steam reformer with a hydrocarbon or methanol reformation catalyst for syngas generation;
installing a separation unit for separating a stream containing carbon dioxide, carbon monoxide and hydrogen into respective streams rich in carbon dioxide, carbon monoxide and hydrogen;
providing for diverting all or part of the syngas stream originally fed to the methanol synthesis loop to the separation unit;
providing for optionally, selectively supplying to the at least one steam reformer in the first mode at least a portion of the carbon dioxide-rich stream and in the second mode at least a portion of the carbon monoxide-rich stream;
providing for optionally supplying in the first mode at least another portion of the carbon dioxide-rich stream to the methanol synthesis loop; and
installing isolation valves for isolating the methanol synthesis loop from the remainder of the converted plant when operated in the second mode.

8. The method of claim 7, wherein the original plant has an ammonia reactor and the method further comprises providing for supplying at least a portion of the hydrogen-rich stream from the separation unit to the ammonia reactor.

9. The method of claim 7, the method further comprising
installing an ammonia reactor for reacting hydrogen and nitrogen to form ammonia;
providing for supplying at least a portion of the hydrogen-rich stream from the separation unit to the ammonia reactor; and
providing a source of nitrogen to the ammonia reactor.

10. The method of claim 7, the method further comprising
installing a CO converter for reacting carbon monoxide and steam to form a shift gas having at least hydrogen and carbon dinoxide; and
providing for supplying at least a portion of the syngas from the at least one steam reformer to the CO converter, wherein the syngas has carbon monoxide and steam.

11. The method of claim 10, the method further comprising
providing for supplying essentially all the syngas to the CO converter; and
providing for supplying the shift gas instead of the syngas to the separation unit.

12. The method of claim 10, the method further comprising
providing for optionally supplying steam to the CO converter.

13. The method of claim 10, the method further comprising
providing for recycling at least a portion of the carbon monoxide-rich stream upstream of the CO converter.

14. The method of claim 7, wherein the separation unit comprises a solvent absorber and stripper for carbon dioxide recovery and a cryogenic distillation unit for carbon monoxide and hydrogen recovery.

15. The method of claim 7, wherein the at least one steam reformer is modified to operate at a higher temperature.

16. A method for operating the converted plant made according to claim 7, the method comprising the steps of:
selecting between the first mode and the second mode of operation; and
operating the converted plant in the selected mode,
wherein the first mode of operation has at least the following steps:
feeding the hydrocarbon to the at least one steam reformer containing the hydrocarbon reforming catalyst,
operating the at least one steam reformer to generate syngas,
separating at least a portion of the syngas stream in the separation unit into respective streams rich in carbon dioxide, carbon monoxide and hydrogen, and
operating the methanol synthesis loop with a feed comprising (1) carbon dioxide and (2) hydrogen to produce methanol, and
wherein the second mode of operation has at least the following steps:
vaporizing the lower alkanol,
feeding the vaporized lower alkanol to the at least one steam reformer, operating the at least one steam reformer to generate syngas, and separating all or part of the syngas stream in the separation unit into respective streams rich in carbon dioxide, carbon monoxide and hydrogen, and isolating the methanol synthesis loop from the remainder of the converted plant.

17. The method of claim 16, wherein the first mode is selected.

18. The method of claim 17, wherein the feed to the methanol synthesis loop comprises imported carbon dioxide.

19. The method of claim 17, wherein the feed to the methanol synthesis loop includes a portion of the syngas.

20. The method of claim 17, wherein essentially all of the syngas stream is supplied to the separation unit.

21. The method of claim 17, wherein the hydrogen supplied to the methanol synthesis loop is provided by supplying at least a portion of the hydrogen-rich stream to the methanol synthesis loop.

22. The method of claim 17, wherein the amount of the hydrogen-rich stream is in excess of the stoichiometric hydrogen required by the methanol synthesis loop.

23. The method of claim 17, wherein essentially all of the carbon dioxide-rich stream is supplied to the methanol synthesis loop.

24. The method of claim 17, wherein carbon dioxide is fed to the at least one steam reformer.

25. The method of claim 24, wherein the carbon dioxide is provided by supplying at least a portion of the carbon dioxide-rich stream from the separation unit.

26. The method of claim 16, wherein steam is fed to the at least one steam reformer.

27. The method of claim 17, wherein
a major portion of the syngas stream is supplied to the separation unit, and
the feed of carbon dioxide and hydrogen to the methanol synthesis loop comprises at least
the carbon dioxide-rich stream from the separation unit,
a minor amount of the syngas stream, and
carbon dioxide from an additional source.

28. The method of claim 17, wherein:
all of the syngas stream is supplied to the separation unit, and
the feed of carbon dioxide and hydrogen to the methanol synthesis loop is selected from:
the carbon dioxide-rich stream from the separation unit,
a minor portion of the syngas stream, and
carbon dioxide from an additional source.

29. The method of claim 16, wherein the second mode is selected.

30. The method of claim 29, wherein the lower alkanol is methanol.

31. The method of claim 29, wherein carbon monoxide is fed to the at least one steam reformer.

32. The method of claim 29 wherein carbon monoxide is fed upstream of a shift converter.

33. The method of claim 32, wherein the carbon monoxide is provided by supplying at least a portion of the carbon monoxide-rich stream from the separation unit.

34. A process for making hydrogen and optionally methanol, the process comprising the steps of:
selecting between a first mode of operation where hydrogen and methanol are produced and a second mode of operation where hydrogen is produced and methanol is not;
reforming a hydrocarbon in a first mode or a lower alkanol in a second mode with steam using a reformation catalyst to form a syngas containing hydrogen, carbon monoxide, and carbon dioxide,
where in the first mode the reforming step is conducted to enhance the production of carbon monoxide and hydrogen and the reformation catalyst is a hydrocarbon reformation catalyst, and
where in the second mode the reforming step is conducted to enhance hydrogen production and the reformation catalyst is selected from the group consisting of hydrocarbon reformation catalyst, methanol reformation catalyst and a combination thereof;
recovering heat from the syngas to form a cooled syngas stream; and
compressing the cooled syngas stream to a separation pressure,
where in the first mode methanol is produced by operating a methanol synthesis loop to react hydrogen with carbon dioxide, and in the second mode the methanol synthesis loop is isolated from the remainder of the process.

35. The process of claim 34, wherein
the first mode is selected,
the process further comprises separating at least a portion of the compressed syngas in a separation unit into a carbon dioxide-rich stream, a carbon monoxide-rich and a hydrogen-rich stream, and
the sources of the hydrogen and carbon dioxide to the methanol synthesis loop are a first portion of the hydrogen from the separation unit and the carbon dioxide from the separation unit.

36. The process of claim 35, wherein additional carbon dioxide from another source is fed to the methanol synthesis loop.

37. The process of claim 34, wherein the first mode is selected and the reforming step is conducted in the presence of carbon dioxide and the syngas produced by the reforming step has a molar R ratio $((H_2-CO_2)/(CO+CO_2))$ from about 2.0 to about 2.9.

38. The process of claim 37, wherein the carbon dioxide present in the reforming step is obtained by recycling the carbon dioxide-rich stream to the reforming step.

39. The process of claim 34, wherein the first mode is selected and the feed to the reforming step has a molar ratio of carbon dioxide to the hydrocarbon comprising natural gas from about 0.1 to about 0.5.

40. The process of claim 34, wherein the first mode is selected and the process further comprises
diverting a major portion of the compressed syngas to a separation unit;
separating the syngas diverted to the separation unit into a carbon dioxide-rich stream, a carbon monoxide-rich stream and a hydrogen-rich stream;
further compressing the remaining minor portion of the syngas to a methanol synthesis pressure higher than the separation pressure; and
operating a methanol synthesis loop to convert the hydrogen, carbon monoxide and carbon dioxide in the further compressed syngas into a methanol stream.

41. The process of claim 40, wherein the methanol synthesis loop is operated substantially below the original design throughput thereof.

42. The process of claim 34, wherein the second mode is selected and the reforming step is conducted to enhance the hydrogen content of the syngas.

43. The process of claim 42, wherein the reforming step is conducted in the presence of carbon monoxide and steam.

44. The process of claim 43, the process further comprising
separating the syngas in the separation unit into a carbon dioxide-rich stream, a carbon monoxide-rich stream and a hydrogen-rich stream.

45. The process of claim 43, wherein the carbon monoxide used in the reforming step is obtained by recycling the carbon monoxide-rich stream to the reforming step.

46. The process of claim 40, wherein the reforming step is conducted in the presence of carbon monoxide and steam.

47. The process of claim 40, the process further comprising reacting the carbon monoxide in the syngas with steam in a shift reaction to form a shift gas having at least carbon dioxide and hydrogen.

48. The process of claim 47, the process further comprising separating the shift gas into a carbon dioxide-rich stream and a hydrogen-rich stream.

* * * * *